United States Patent [19]

Onoda et al.

[11] Patent Number: 5,058,597
[45] Date of Patent: Oct. 22, 1991

[54] LONG-TERM ELECTROCARDIOGRAPH FOR SCREENING

[75] Inventors: Masahiro Onoda; Tadashi Fujii, both of Nakai, Japan

[73] Assignee: Terumo Kabushiki Kaisha, Tokyo, Japan

[21] Appl. No.: 510,184

[22] Filed: Apr. 17, 1990

[30] Foreign Application Priority Data

Apr. 27, 1989 [JP] Japan .................................. 1-105927

[51] Int. Cl.⁵ .............................................. A61B 5/04
[52] U.S. Cl. .................................... 128/696; 128/704; 128/708
[58] Field of Search ................ 128/696, 704, 708, 702

[56] References Cited

U.S. PATENT DOCUMENTS

| | | | |
|---|---|---|---|
| 3,267,934 | 8/1966 | Thornton | 128/704 |
| 3,495,584 | 2/1970 | Schwalm | 128/696 |
| 3,868,567 | 2/1975 | Ekstrom | 128/704 |
| 4,000,461 | 12/1976 | Barber et al. | 128/708 |
| 4,546,776 | 10/1985 | Bellin et al. | 128/704 |

Primary Examiner—Francis Jaworski
Assistant Examiner—George Manuel
Attorney, Agent, or Firm—Staas & Halsey

[57] ABSTRACT

An electrocardiograph has an R wave detector for detecting an R wave out of an electrocardiogram (ECG) signal being collected from a subject. When the R wave detector detects an R wave, a heart rate and an ST value of the ECG signal are written to a storage which is assigned to heart rates and ST values in synchronism with the R wave. When the subject presses an event switch on feeling a subjective symptom, the waveform of the ECG signal is written to another storage which is assigned to waveforms. The electrocardiograph records a minimum necessary amount of information for screening, i.e., the heart rates, ST values, and waveforms of ECG signal associated with subjective symptoms. The electrocardiograph is, therefore, miniature and easy to carry while reducing the period of time necessary for analysis.

9 Claims, 10 Drawing Sheets

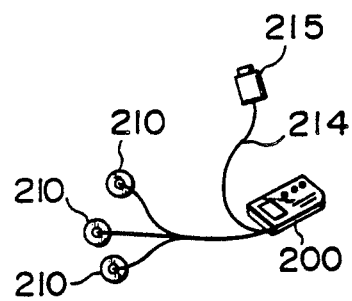
FIG. 2
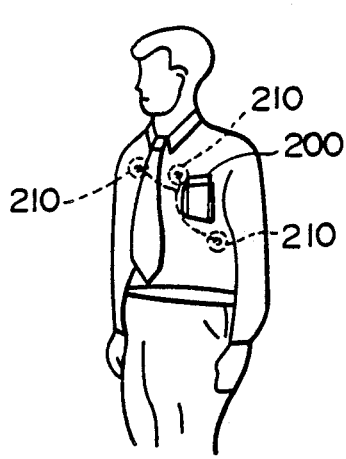
FIG. 3
FIG. 4
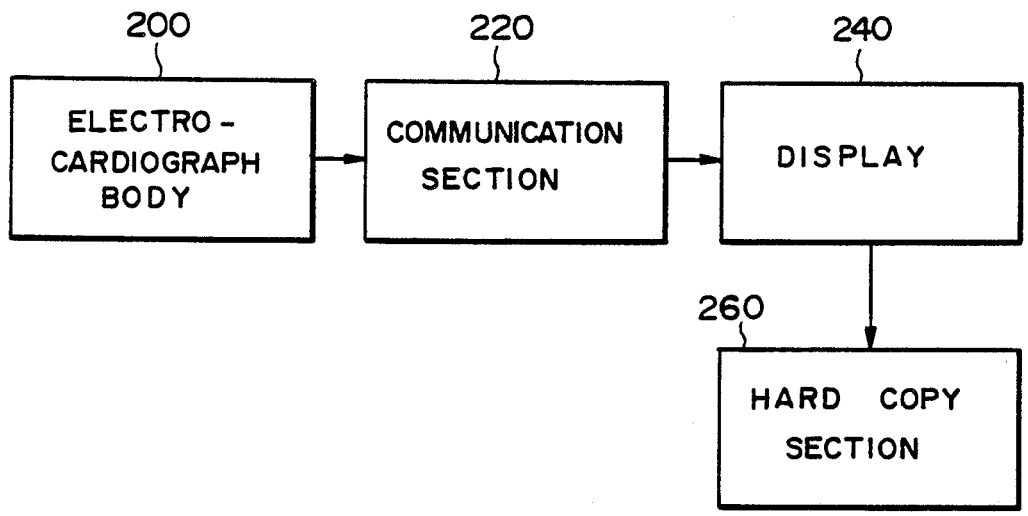

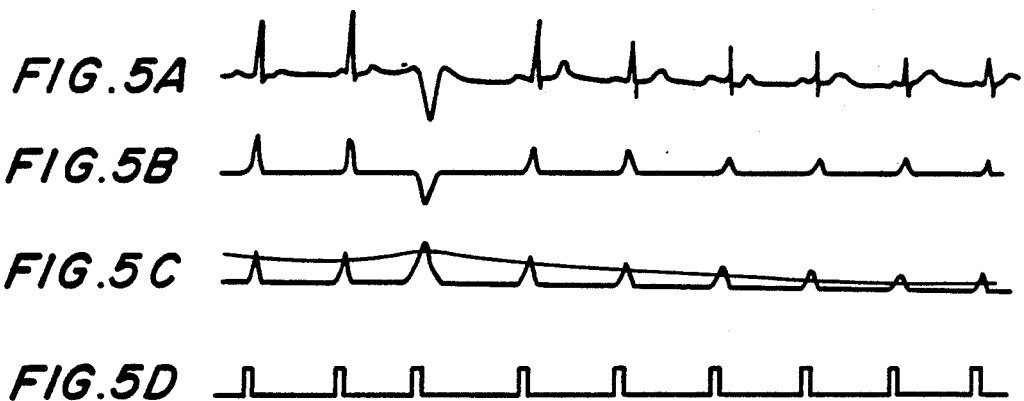
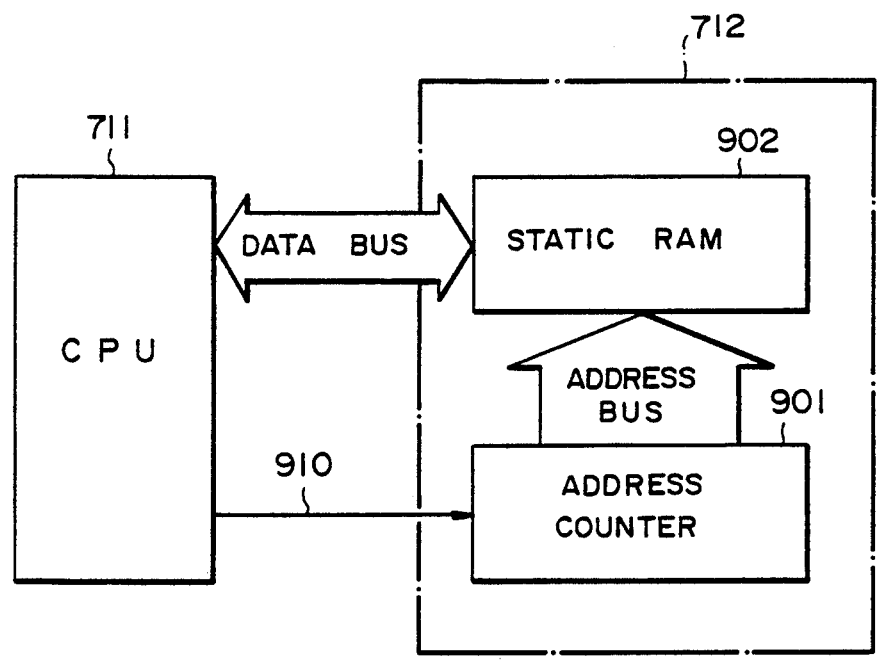

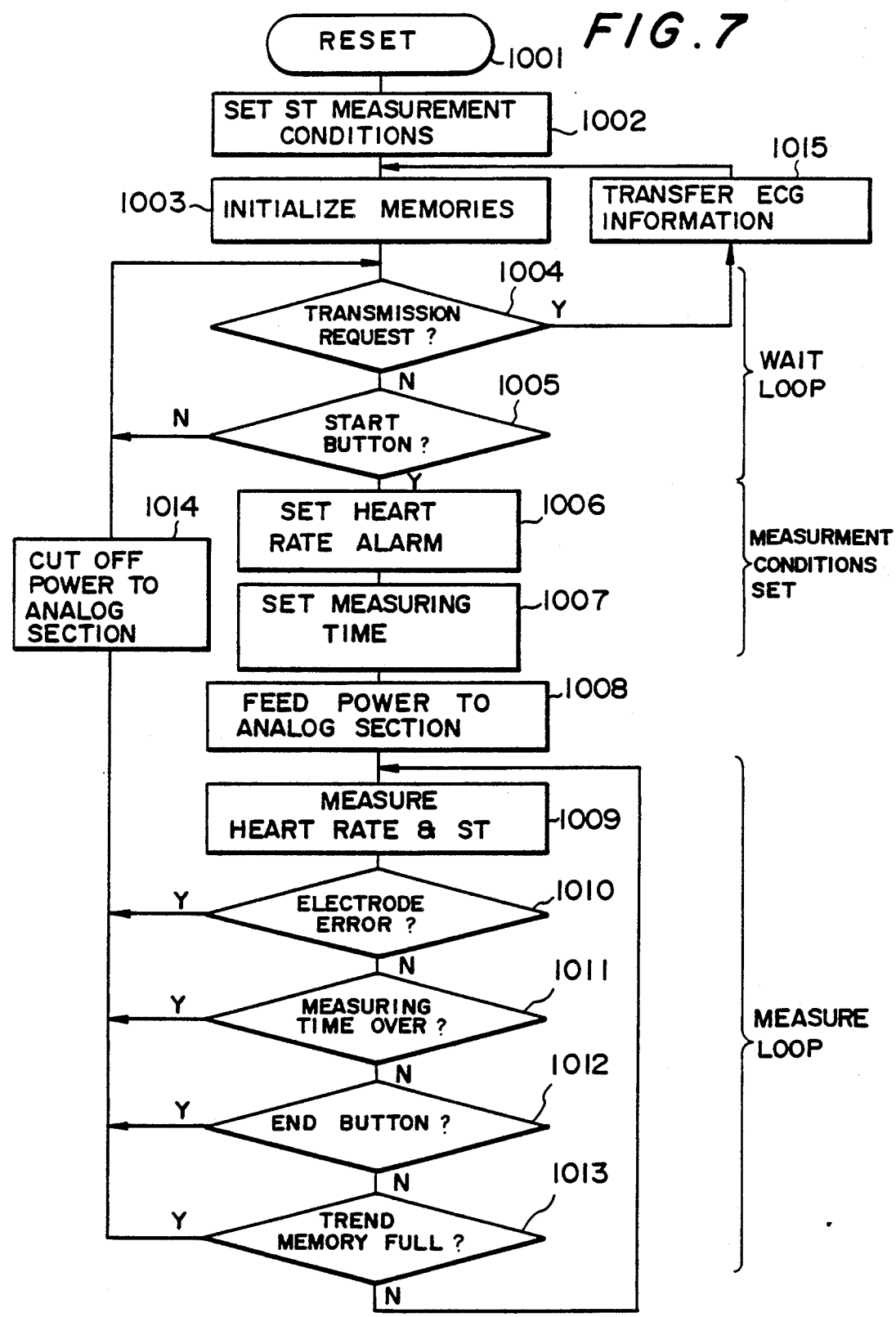

MOMENTARY HEART RATE TRENDGRAM

FULL ECG WAVEFORM

HEART RATE TREND

ST TRENDGRAM

EVENT MARK WAVEFORM

ARRHYTHMIA WAVEFORM

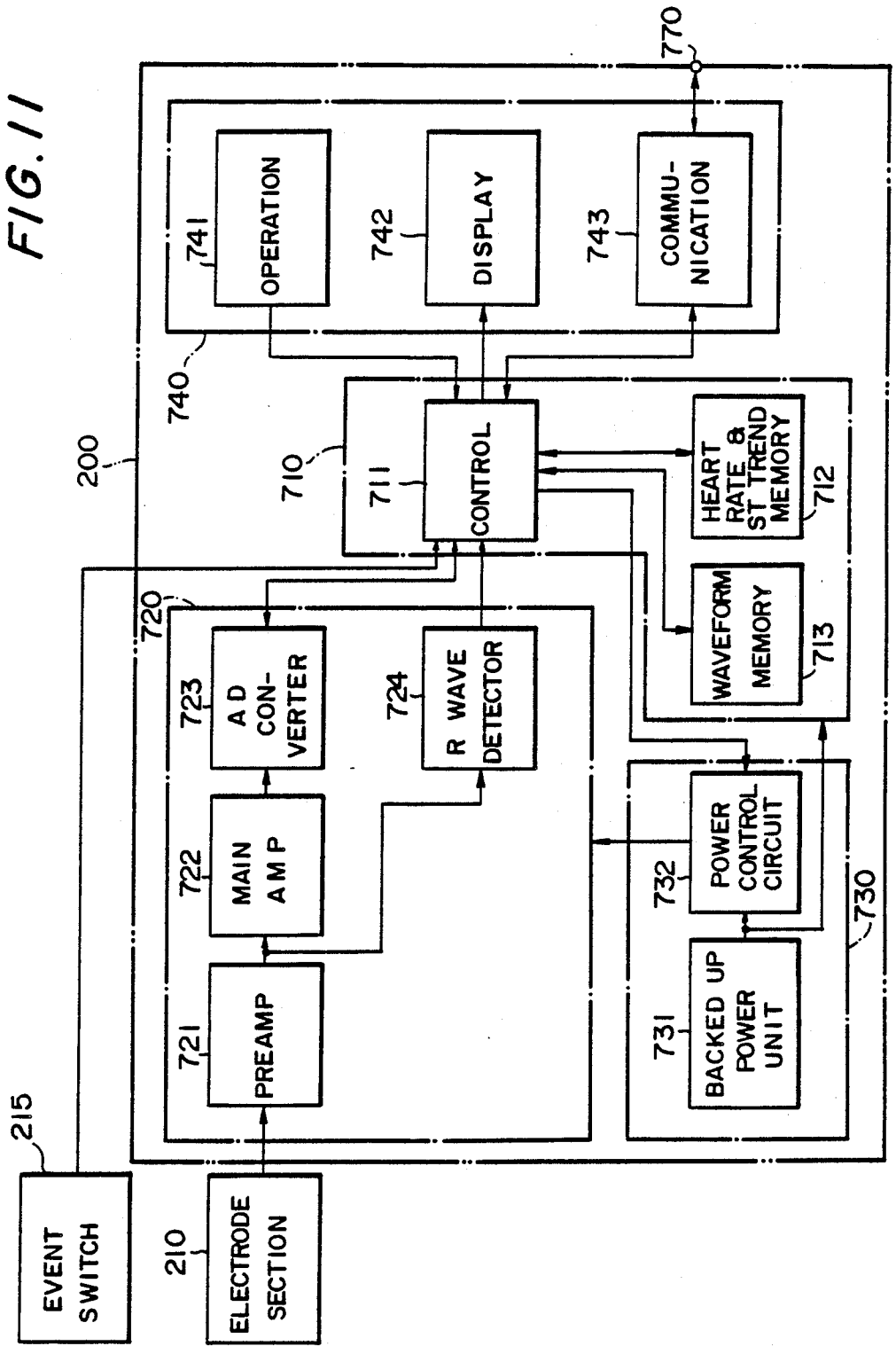

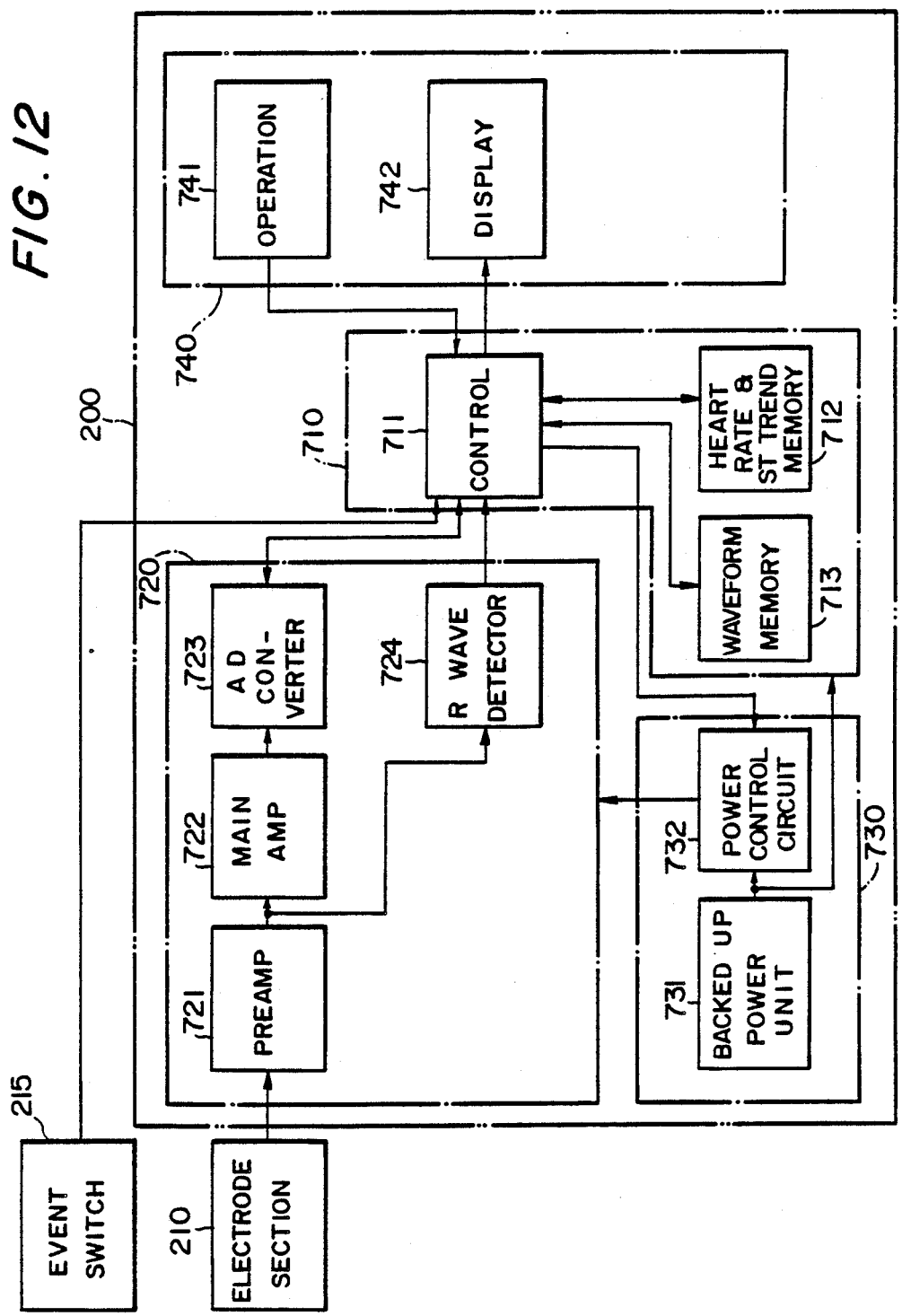

LONG-TERM ELECTROCARDIOGRAPH FOR SCREENING

BACKGROUND OF THE INVENTION

1. Field of the Invention

The present invention relates to an electrocardiograph which promotes easy measurement of an electrocardiogram (ECG or, more commonly EKG) over a long period of time while being carried by a subject.

2. Description of the Prior Art

In the modern medical services field, a clinical examination for measuring an ECG and a blood pressure, for example, is a common practice. Usually, this kind of examination is conducted within quite a limited period of time in a medical care institution such as a clinic or a hospital under the control of a medical doctor or an examiner or inspector of the clinical check. However, there are diseases which cannot be detected by the automatic examination effected in a short period of time as stated above. Temporary disorder of the heart or arrhythmia, for example, often escapes the operator's attention during the examination because an unusual wave does not always clearly appear in an ECG. In many cases, therefore, it is difficult to give a determinant diagnosis through such a short time of examination.

In order to detect arrhythmia or similar disease of the kind described, there has been proposed a method for measuring an ECG over a long period of time. This method is implemented by a long-term ECG or so-called Holter ECG. Specifically, a portable electrocardiograph is put on the body of a subject of examination throughout the day or 24 hours in the daily life so as to collect and record electrocardiographic waveforms on a magnetic tape. Afterwards, while the waveforms are reproduced by a magnetic playback apparatus, an inspector such as a medical doctor observes it to find abnormality out of the waveforms and thereby conducts a diagnosis of disease such as a fugitive affection of the heart.

The electrocardiographic waveforms recorded on a magnetic tape as stated above are great in amount and, therefore, reproduced at a high speed. A problem with this prior art implementation is, therefore, that the inspector has to give a diagnosis by reading such a great amount of waveforms which are being reproduced at a high speed. Reproducing all the electrocardiographic waveforms collected over 24 hours and analyzing them by consuming a long period of time involves much wasteful work when it comes to arrhythmia which is transitory and rarely appears, resulting in low inspection efficiency as a whole.

To solve the above problem, there has also been proposed a system wherein while a magnetic tape recorded with a great amount of waveforms is reproduced at a high speed (60 times or 120 times the ordinary playback speed), an apparatus analyzes the waveforms automatically by a predetermined procedure and displays only particular portions thereof which is determined to be unusual. With this implementation, an inspector has only to examine the abnormal portions of the waveforms. However, since the electrocardiographic waveform data sequentially read out of the magnetic tape are fed to an exclusive microcomputer for analysis at a high speed due to the high-speed playback, a sufficiently long period of time cannot be allocated to the microcomputer analysis. Hence, the accuracy of analysis achievable with this scheme is limited.

A method elaborated to enhance accurate analysis has been reported recently. This method collects an ECG over a long period of time and, at the same time or on a real time basis, analyzes electrocardiographic waveforms automatically. Only the waveforms which were determined to be unusual are recorded on a magnetic tape, IC memory, or similar storage. Afterwards, only the unusual waveforms and the result of analysis are reproduced on a display which is located at the doctor's side. The doctor may print out such data for confirmation, if necessary. With this kind of approach, it is possible to allocate a 60 times or a 120 times longer period of time to the analysis than with the previously stated approach.

With the long-term and real-time analysis scheme, it is not that all the electrocardiographic waveforms collected over 24 hours are recorded but that only the waveforms determined to be unusual by the automatic analysis are recorded, as discussed above. Stated another way, the waveforms determined to be normal by the automatic analysis are simply discarded. This brings about a problem that abnormal waveforms which may have occurred in the discarded waveforms escape the doctor's attention. A prerequisite with the real-time analysis is, therefore, that abnormal waveforms be prevented from being overlooked. Also, preventing normal waveforms from being determined unusual is an important consideration in the aspect of the time and labor which would be consumed for the inspection. However, since electrocardiograhic waveforms suffer from the difference between individuals, determining whether or not they are normal by using a fixed criterion tends to increase the error rate.

As discussed above, the prior art Holter electrocardiograph needs much time and labor for examination. The apparatus is too large and heavy for a subject to carry it all through the day while dealing with routine work, imposing heavy loads on the subject both physically and mentally. Moreover, such an apparatus is expensive. While the real-time analysis type Holter electrocardiograph is successful in eliminating the problem concerning the examination or analysis time, it is not satisfactory in the aspect of reliability or accuracy of analysis and is as large and heavy as the conventional Holter electrocardiograph, again effecting the subject physically and mentally.

Recently, apparatuses capable of detecting a transitory cardiac disease by a simple procedure while reducing the loads of the subject have been reported. One of them is constructed such that when the subject feels palpitation, short of breath, vertigo or similar symptom, the subject puts the apparatus on the chest to record an ECG. Afterwards, the apparatus with the ECG is brought to a doctor and connected to an electrocardiograph to output electrocardiographic waveforms. Although this kind of apparatus is easier to carry than the conventional apparatuses, relying on the symptoms of which the subject will be conscious is problematic because an arrhythmia is not always accompanied by a subject symptom. Another problem is that the apparatus cannot always seize the decisive moment due to the interval between the time when the subject feels the symptom and the time when the subject actually puts the apparatus on the chest (the apparatus has to be pressed against the skin). Moreover, the recording time available with such an apparatus is extremely short (not longer than 1 minute) so that one may feel it awkward to go and see a doctor for the analysis of such a short ECG.

A heartbeat gauge is a further simpler apparatus recently developed in various forms. For example, the heartbeat gauge is provided with a writstwatch type configuration and has a photosensor thereinside. When the subject presses any one of the fingers against the gauge, the gauge displays a pulse frequency which the photosensor senses. Another heartbeat gauge is implemented as a wristwatch type body and a sack which has a photosensor therein and is interconnected to the body by a cable. The sack is put on the tip of a subject's finger for sensing pulses, while the body displays the pulse frequency. Still another heartbeat gauge is made up of a belt in which electrocardiographic electrodes are built in, and a wristwatch-like body. The belt is put on the subject's chest to sense the heartbeats and transmits the heart rate to the body by radio, while the body displays the heart rate. All of such gauges, however, simply display the pulse frequency or the heart rate and do not contribute to the detection of a cardiac disorder.

SUMMARY OF THE INVENTION

It is therefore an object of the present invention to provide a portable electrocardiograph which imposes a minimum of load on the subject, promotes easy screening of a disorder of the heart, and is reliable and economical.

A long-term electrocardiograph for screening of the present invention comprises an inputting section for collecting an ECG signal from a subject, and an R wave detecting section for detecting an R wave out of the ECG signal collected by the inputting section. The electrocardiograph further comprises an ECG signal processing circuit for processing the ECG signal in response to an R wave detection signal generated by the R wave detecting section, and a heartbeat and ST trend storage for storing a heart rate and an ST value of the ECG signal. The ECG signal processing circuit causes the heartbeat and ST trend storage to store time-serially a heart rate and an ST value obtained from the ECG signal.

In accordance with the present invention, information associated with a heartbeat trendgram and an ST trendgram are produced by processing the ECG signal in synchronism with the R wave detection signal and are recorded in the heartbeat and ST trend storage. The electrocardiograph having the above construction is miniature and light weight and simplifies the screening of a cardiac disorder.

BRIEF DESCRIPTION OF THE DRAWINGS

The objects and features of the present invention will become more apparent from the consideration of the following detailed description taken in conjunction with the accompanying drawings in which:

FIG. 2 is a perspective view of the electrocardiograph shown in FIG. 1;

FIG. 3 is a sketch showing a specific condition wherein the electrocardiograph of FIG. 1 is used;

FIG. 4 is a block diagram schematically showing a procedure which will be executed after the measurement of an ECG with the illustrative embodiment;

FIGS. 5A to 5D are waveforms demonstrating how R waves are detected;

FIG. 6 is a block diagram schematically showing the structure of a sequential buffer which implement a trend memory shown in FIG. 1;

FIG. 7 is a flowchart representative of a specific operation of the illustrative embodiment;

FIGS. 11, 12 and 13 are schematic block diagrams each showing a different alternative embodiment of the present invention.

DESCRIPTION OF THE PREFERRED EMBODIMENTS

Figure 1:
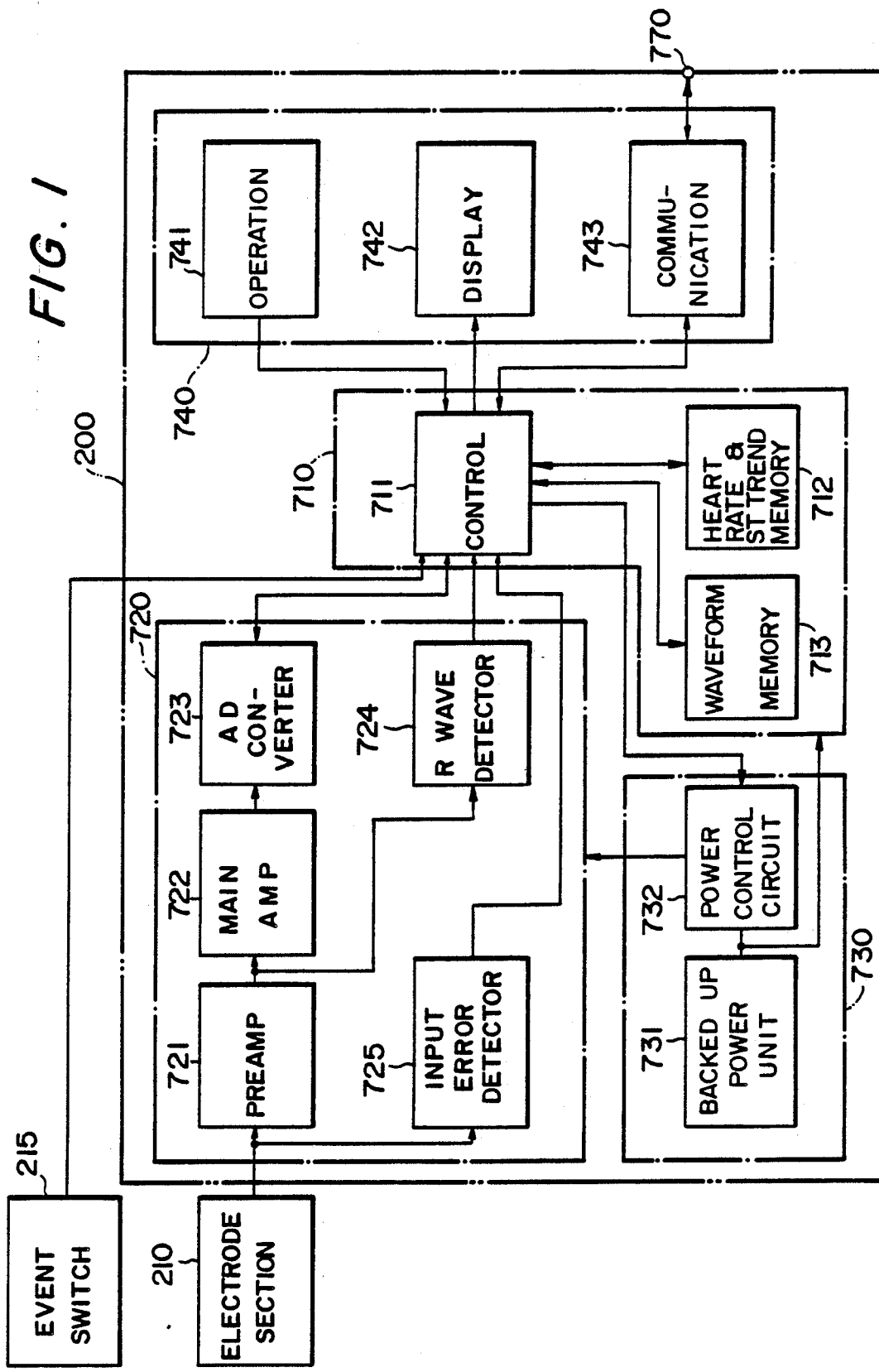
FIG. 1 is a block diagram schematically showing an embodiment of the portable electrocardiograph in accordance with the present invention.

Referring to FIGS. 1 to 4 of the drawings, a long-term electrocardiograph embodying the present invention is shown. As shown in FIG. 1, the electrocardiograph is generally made up of a body 200, an electrode section 210, and an event switch 215. The electrode section 210 serves as inputting means to which an ECG signal is fed from the subject's body. The event switch 215 plays the role of operating means which is to be operated when the subject feels palpitation, short breath, vertigo or similar cardiac symptom.

In the illustrative embodiment, the body 200 has a card size and is small and light enough to be put in the subject's chest pocket, for example, as shown in FIG. 3. The electrode section 210 is removably affixed to the subject's chest and abdomen according to a predetermined induction method. The event switch 215 is clipped to a position where the subject can readily press it, although not shown in FIG. 3. While the event switch 215 is shown as being interconnected to the body 200 by a cord 214 in FIG. 2, it may alternatively be mounted on the surface of the body 200.

While the subject carries the body 200 of the electrocardiograph for a predetermined period of time (usually, 24 hours or so), the electrocardiograph measures an ECG, as shown in FIG. 3. Thereafter, the subject removes the body 200 and electrode section 210 and then connects the body 200 to a communicating section 220, as shown in FIG. 4. In this condition, the electrocardiographic data recorded in the body 200 is transferred to a display 240 via the communicating section 220. The electrocardiographic data is shown on the display 240 and, if necessary, fed to a hard copy section 260 to produce a hard copy (recording).

FIGS. 9A to 9E indicate typical examples of electrocardiographic information, i.e., full electrocardiographic waveforms (compressed waveforms) 500, a heart rate trend 510, an ST trend 520, an event marking waveform 530, and an arrhythmical waveform 540. Since such electrocardiographic information collected over 24 hours is extremely great in amount, examining them throughly, especially the full electrocardiographic waveforms, needs much time and labor. This is one of the major causes of the decrease in the efficiency of examination. Although examining a 24 hours ECG with scrupulous care will be a requisite when it is intended for close diagnosis (examination), it contains an excessive amount of information when it comes to screening, i.e., more than necessary amount of electrocardiographic information is recorded and outputted.

In light of the above, various attempts have been made to accomplish screening with a minimum necessary amount of electrocardiographic information. For example, it was presented in "Role of Holter Electrocardiographic Information in The Detection of Arrhythmia", 25th Meeting of the Institute of Medical Electronics Engineers of Japan, Lecture 3-B-15 (Apr. 1986), that only two kinds of electrocardiographic information, i.e., a momentary heart rate trendgram and a momentary ST trendgram suffice for the diagnosis of an arrhythmia which frequently occurs. This presentation was reported to have been based on 2,500 clinical tests. Considering this report, the present invention deals with only three kinds of electrocardiographic information, i.e., a heart rate trendgram, an S. T. trendgram, and an event marking waveform.

By limiting the electrocardiographic information to be recorded to those which are necessary for screening examinations as stated above, it is possible to reduce the required capacity for recording information substantially, compared to the prior art Holter electrocardiograph. Hence, a cassette type magnetic tape having a great recording capacity and customarily used as a recording medium can be replaced with a semiconductor memory. This in turn allows the entire electrocardiograph to be implemented by semiconductor and thereby renders the electrocardiograph small in size, light in weight, and easy to carry.

Referring again to FIG. 1, the body 200 of the portable electrocardiograph is made up of a control and record section 710, an analog section 720, a power source section 730, and an interface section 740. The analog section 720 has a preamplifier 721, a main amplifier 722, an analog-to-digital (AD) converter 723, an R wave detector 724, and an input error detector 725.

The preamplifier 721 amplifies faithfully AC components included in an ECG signal which is generated by the electrode section 210. The electrode section 210 is affixed to the subject's chest and abdomen according to a predetermined induction method, as stated earlier. Specifically, the preamplifier 721 is composed of two circuits, i.e., an operational amplifier and a DC cut-off filter which are interconnected in this order, although not shown in the figure. The operational amplifier has an input resistance as high as 1 megaohm or above so as to amplify the signal from the electrode section 210 without being affected by the resistance of the living body, which is several kiloohms. Further, the operational amplifier serves to cancel in-phase noise introduced in the electrode section 210. The DC cut-off filter removes DC voltage components ascribable to the polarization of electrodes which are included in the electrode section 210. Preferably, the cut-off frequency of the DC cut-off filter is lower than 0.05 Hertz so as not to influence the ECG signal.

The main amplifier 722 amplifies the output ECG signal of the preamplifier 721 to a level which is necessary for the AD converter 723 to convert the analog ECG signal to a digital signal. The AD converter 723 transforms the amplified analog ECG signal to a digital ECG signal in response to a conversion request which may be fed thereto from the control and record section 710, more specifically a control subsection 711 included therein as will be described. The digitized signal from the AD converter 723 is applied to the control subsection 711.

Figure 14:
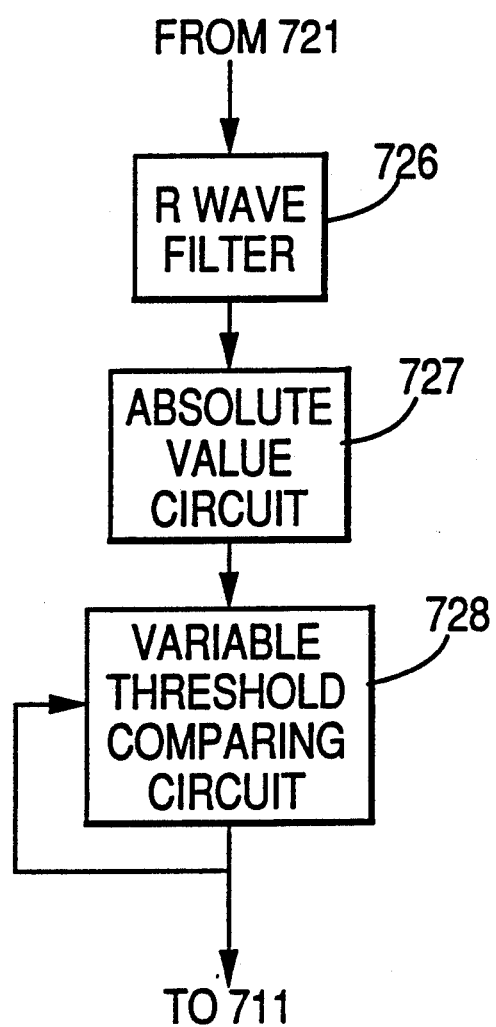
FIG. 14 is a block diagram of an R wave detector.

The R wave detector 724, illustrated in FIG. 14, detects an R wave which is the most characteristic waveform of an ECG. The output of the R wave detector 724 representative of an R wave is also fed to the control 711. Applied to the R wave detector 724 is the output signal of the preamplifier 721 or that of the main amplifier 722. The R-wave detector 724 is constituted by an R wave filter 726, an absolute value circuit 727, and a variable threshold comparing circuit 728 which are interconnected in this order. Such circuitry allows the portable electrocardiograph to detect R waves accurately at all times despite that the waveforms of an ECG greatly depend on the individual.

Specifically, the R wave filter 726 mentioned above selectively passes only the R waves which appear in the ECG signal. The absolute value circuit 727 regulates the amplitudes the R waves to only one direction in order to accommodate both positive and negative amplitudes. While an R wave is detected when the ECG signal routed through the R wave filter 726 and absolute value circuit 727 exceeds a certain threshold, its amplitude not only differs from one person to another but also changes moment by moment within the same person. The variable threshold comparing circuit 728 serves to automatically change the threshold in association with the amplitude of the R wave and to compare the output signal of the absolute valve circuit 727 with the variable threshold.

FIGS. 5A to 5D indicate a procedure which the R wave detector 724 executes for detecting R waves. Specifically, FIG. 5A shows an input signal to the R wave detector 724, while FIG. 5B shows an output signal of the R wave filter. FIG. 5C is representative of an output signal of the absolute value circuit along with the variation of the threshold. FIG. 5D indicates the resultant output signal of the R wave detector 724.

The input error detector 725 is responsive to various kinds of faults which may occur in the electrode section 210, i.e., separation between the skin and the electrodes, disconnection and other similar connection errors of the inputting section. On detecting such a fault, the input error detector 725 sends an error signal to the control 711. As shown in FIG. 1, the electrode error detector 725 receives a signal directly from the electrode section 210. Alternatively, an arrangement may be made such that the detector 725 detects an error out of the output signal of the preamplifier 721 or that of the main amplifier 722.

The control and record section 710 has a trend memory 712 and a waveform memory 713 in addition to the control section 711. The interface section 740 has an operation section 741, a display section 742, and a communication section 743. The control section 711 is implemented by an ultra-low power consumption type 4-bit 1-chip microcomputer, for example, and constitutes the heart of the portable electrocardiograph in the control aspect. The microcomputer serving as the control section 711 has a PROM, RAM, liquid crystal display driver, timer, communication interface, I/O port built in a 1-chip integrated circuit. The operation section 741 has a group of switches accessible to the subject for starting and ending a measurement and for setting measurement conditions which will be described. The display section 742 is implemented as a liquid crystal display (LCD) for displaying operating conditions and of a low power consumption type. The communication section 743 functions as an interface for transferring recorded electrocardiographic information to the display 240 (FIG. 4) which is independent of the portable electrocardiograph. These sections are controlled by using the functions of the I/O ports, LCD driver and communication interface available with the control section 711, thereby enhancing the miniaturization of the apparatus.

Figure 10:
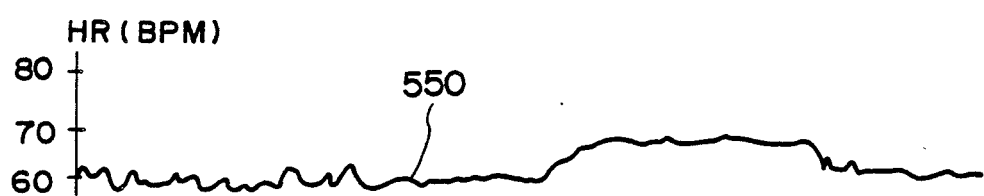
FIG. 10 shows a momentary heart rate trend.
Figure 9A:
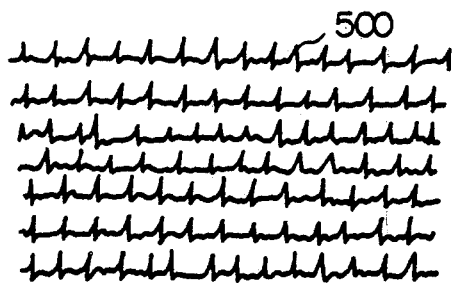
FIGS. 9A to 9E show respectively an electrocardiographic waveform, a heart rate trendgram, an ST trendgram, an event marking waveform, and an arrhythmia waveform.
Figure 9B:
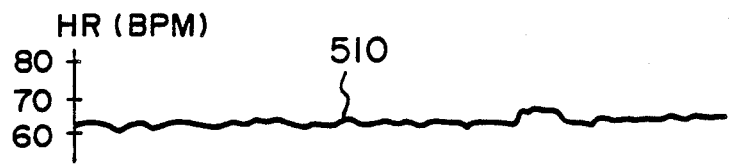
Figure 9C:
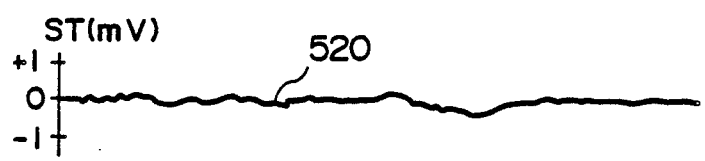
Figure 9D:
Figure 9E:
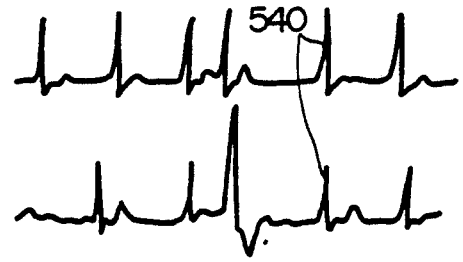

As stated previously, the present invention records three kinds of electrocardiographic information, i.e., a momentary heart rate trendgram 550 shown in FIG. 10 and the ST trendgram 520 and event marking waveform 530 shown in FIGS. 9C and 9D. The heart rate and ST trend memory 712 is assigned to the mementary heart rate trendgram 550 and momentary ST trendgram 520. Momentary heart rate data and momentary ST data are calculated in synchronism with the detection signal from the R wave detector 724 by program which is stored in the control section 711. These calculated data are written to the heart rate and ST trend memory 712 as a set of data. Each of the momentary heart rate trend data and the momentary ST trend data is time-serial data. Characteristically, the heart rate and ST trend memory 712 for recording such time-serial data has a sequential buffer type structure, as shown in FIG. 6. Specifically, the memory 712 is composed of an address counter 901 and a low power consumption type static RAM 902. An address count signal line 910 is connected to the control, or CPU, 711. In this configuration, the CPU 711 controls the address count signal line 910 to designate the read/write addresses of the memory 712. Such a sequential buffer structure noticeably reduces the number of address lines which the CPU 711 has to control.

The waveform memory 713 is assigned to the event marking waveform 530. An event will be marked when the subject operates the event switch 215 on feeling a palpitation, short breath, vertigo or similar subjective symptom. The interval between the development of a subjective symptom and the operation of the event switch 215 is critical, as discussed earlier. In the illustrative embodiment, the waveform memory 713 is provided with a ring buffer structure so that it may start recording an electrocardiographic waveform 8 seconds before the operation of the event switch 215 as an event marking waveform. The ring buffer structure is equivalent to the sequential buffer structure shown in FIG. 6, except that on counting over the address counter 901 is reset to zero and then starts counting again. It is to be noted that the recording time available with the waveform memory 713 as mentioned above is determined by the size of the ring buffer, i.e., the recording time of 8 seconds is only illustrative and simply derived from the technical limitations of a memory. In this embodiment, the waveform memory 713 has sixteen ring buffers for recording the event marking waveform 530 and, therefore, can record up to sixteen event marking waveforms. Again, the specific number of ring buffers "sixteen" is derived from the technical limitations of a memory and may be increased, if desired.

The electrocardiographic waveforms shown and described may be recorded in a higher density by using a suitable compression coding technology such as a SAPA compression method or a delta coding method.

The power source section 730 has a power source unit 731 which is backed up and a power source control circuit 732. The power source unit 731 is a power source circuit which uses a main battery and a back-up battery. When the voltage of the main battery is lowered beyond a predetermined voltage or when the main battery is to be replaced, the power supply source is automatically switched from the main battery to the back-up battery to maintain a predetermined output voltage at all times. The power source control circuit 732 is implemented as a power switch which is electrically controlled by the control 711. The supply of power to the analog section 720 is effected via the power source control circuit 732. The control 711 controls the power source control circuit 732 in the event of a measuring operation only, thereby powering the analog section 720. The control and record section 710 is directly powered by the power source unit 731 so as to remain operative all the time.

The operation of the portable electrocardiograph having the above construction will be described with reference to FIG. 7.

When the power switch of the electrocardiograph is turned on for the first time, the control 711 is automatically reset (step 1001) to start executing the program. First, the control 711 sets ST measurement conditions (step 1002) and then initializes the memories (step 1003). The step 1002 for setting ST measurement conditions is executed only when the control 711 is in a reset condition.

Figure 8:
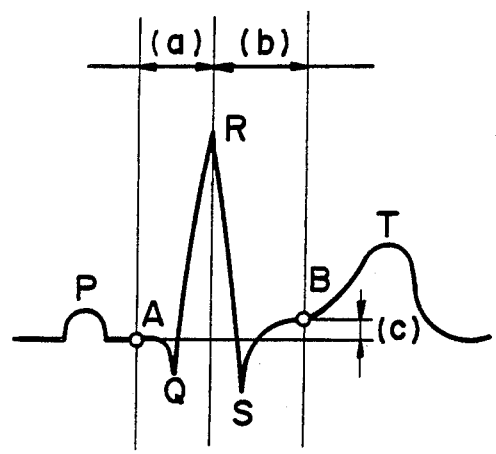
FIG. 8 shows an electrocardiographic waveform representative of a single heart rate.

FIG. 8 shows an electrocardiographic waveform representative of a single heartbeat. As shown, the waveform has characteristic points P, Q, R, S and T. A point B between the characteristic points S and T and a point A between the characteristic points P and Q have a level difference (c) which will be referred to as an ST level. An operation for measuring this level difference (c) will be called an ST measurement. The points A and B are respectively defined as a point 40 milliseconds to 80 milliseconds ahead of the characteristic point R (interval (a), FIG. 8) and a point 80 milliseconds to 120 milliseconds past of the characteristic point R (interval (b), FIG. 8). The intervals (a) and (b) of FIG. 8 are the ST measurement conditions to be selected in the step 1002 and which are selected within the individual ranges mentioned above.

In the step 1003, both the trend memory 712 and the waveform memory 713 are initialized, i.e., their contents are deleted. The trend memory 712 having a sequential buffer structure has its write address initialized to the leading end of the sequential buffer, while the waveform memory 713 implemented by a plurality of ring buffers has its write address initialized to the leading end of the first ring buffer. After the initialization, the program enters into a wait loop in which the detection of a communication request (step 1004) and the detection of the operation of a start button (step 1005) are repeated. While the wait loop is executed, the contents of the trend memory 712 and waveform memory 713 are backed up and the total power consumption by the electrocardiograph is reduced.

When the start button is operated as detected in the step 1005, a measurement begins. Specifically, a heart rate alarm and a measuring time are sequentially set in this order (steps 1006 and 1007) as measurement conditions. In the illustrative embodiment, the electrocardiograph has a function of generating an alarm when the heart rate exceeds a predetermined upper limit or a predetermined lower limit while in measurement. Setting the heart rate alarm as stated in relation to the step 1006, therefore, refers to the setting of the above-mentioned upper and lower limits or the cancellation of the alarm function. Another function available with the illustrative embodiment is to cause the measurement to be automatically stopped by a timer. Setting a measuring time as effected in the step 1007, therefore, refers to setting the time of the timer or cancelling the timer function.

After the various measurement conditions have been set, the power source control circuit 732 is controlled ON to feed power to the analog section 720 (step 1008). This is followed by a measurement loop which comprises the measurement of the heart rate (step 1009) and four successive comparison steps associated with the input error, the end of measuring time, end button, and trend memory full (steps 1010 to 1013). The heart rate and ST measurement in the step 1009 is continued until any one of the results of decision associated with the above-mentioned four different conditions turns to YES.

Specifically, the result of decision associated with the input error, or step 1010, becomes YES when the input error detector 725 detects a fault in the electrode section 210. The result of the step 1011 associated with the end of measuring time turns to YES when the automatic measurement stop function available with the timer has been selected in the step 1007 and the set time is over. The result of the step 1012 associated with the end button becomes YES when the subject presses a stop button. Further, the result of the step 1013 associated with the trend memory full turns to YES when the trend memory 712 is filled up.

The heart rate and ST measurement effected in the step 1009 is the major part of the measurement processing of the illustrative embodiment. The measurement is such that a momentary heart rate and a momentary ST value are measured in synchronism with the detection output of the R wave detector 724 and written to the trend memory 712 as a set of data. Simultaneously, a mean value of four to eight heartbeats occurred up to the present time is displayed on the display subsection 742 by using the liquid crystal display driver of the control 711.

The measurement loop is followed by a step 1014 for cutting off the power supply to the analog section 720. The program returns to the wait loop via the step 1014. Specifically, in the step 1014, the power control unit 732 is controlled OFF to interrupt the supply of power to the analog section 720. In this manner, the power supply to the analog section 720 is set up only when the measurement loop is under way. This is successful in reducing the overall power consumption of the apparatus and, therefore, in miniaturizing the power source with backed up power unit 731.

When a communication request arrives as detected in the step 1004 of the wait loop, the electrocardiographic information is transferred (1015). The transmission request appears after the body 200 of the electrocardiograph has been connected to the display 240 via the communication section 220, as shown in FIG. 4. In response to the communication request, a step 1015 is executed for transferring to the display 240 the electrocardiographic information which have been recorded in the trend memory 712 and waveform memory 713 by the previously stated measurement loop. On completing the transfer of such information, the program returns to the step 1003 to initialize the trend memory 712 and waveform memory 713.

One of characteristics of the illustrative embodiment is that after the measurement loop the electrocardiograph can resume the measurement without transferring the electrocardiographic information to the display 240.

When the measurement is resumed, the resulting information is recorded after the information having been collected up to the present time. Such a repetitive measurement can be executed until the trend memory 712 becomes full. This kind of function may be referred to as a postscript function.

Although not shown in the flowchart of FIG. 7, when the event switch 215 is pressed while the measurement loop is under way, the instantaneous electrocardiographic waveform will be collected by interrupt control. Specifically, on the operation of the event switch 215, a waveform having been stored in one of the ring buffers which constitute the waveform memory 713 is saved in that ring buffer by a predetermined amount associated with eight seconds up to the time when the event switch 215 is operated. Thereafter, an empty ring buffer is selected to load it with a new waveform in an endless fashion to prepare for the future collection of an event waveform. As soon as all the ring buffers become full, the processing for collecting a waveform at the time of an event is inhibited.

Referring to FIG. 11, an alternative embodiment of the present invention is shown. This embodiment differs from the embodiment of FIG. 1 in that it lacks the input error detector 725 and, therefore, the function of interrupting the heart rate and ST measurement on detecting an error of the electrodes.

FIG. 12 shows another alternative embodiment of the present invention in which the communication section 743 of the embodiment shown in FIG. 11 is omitted. This embodiment, therefore, does not have the function of sending the heart rate and ST value and the waveform signal recorded in the waveform memory to external display means when the electrocardiograph is connected to the display means.

Figure 13:
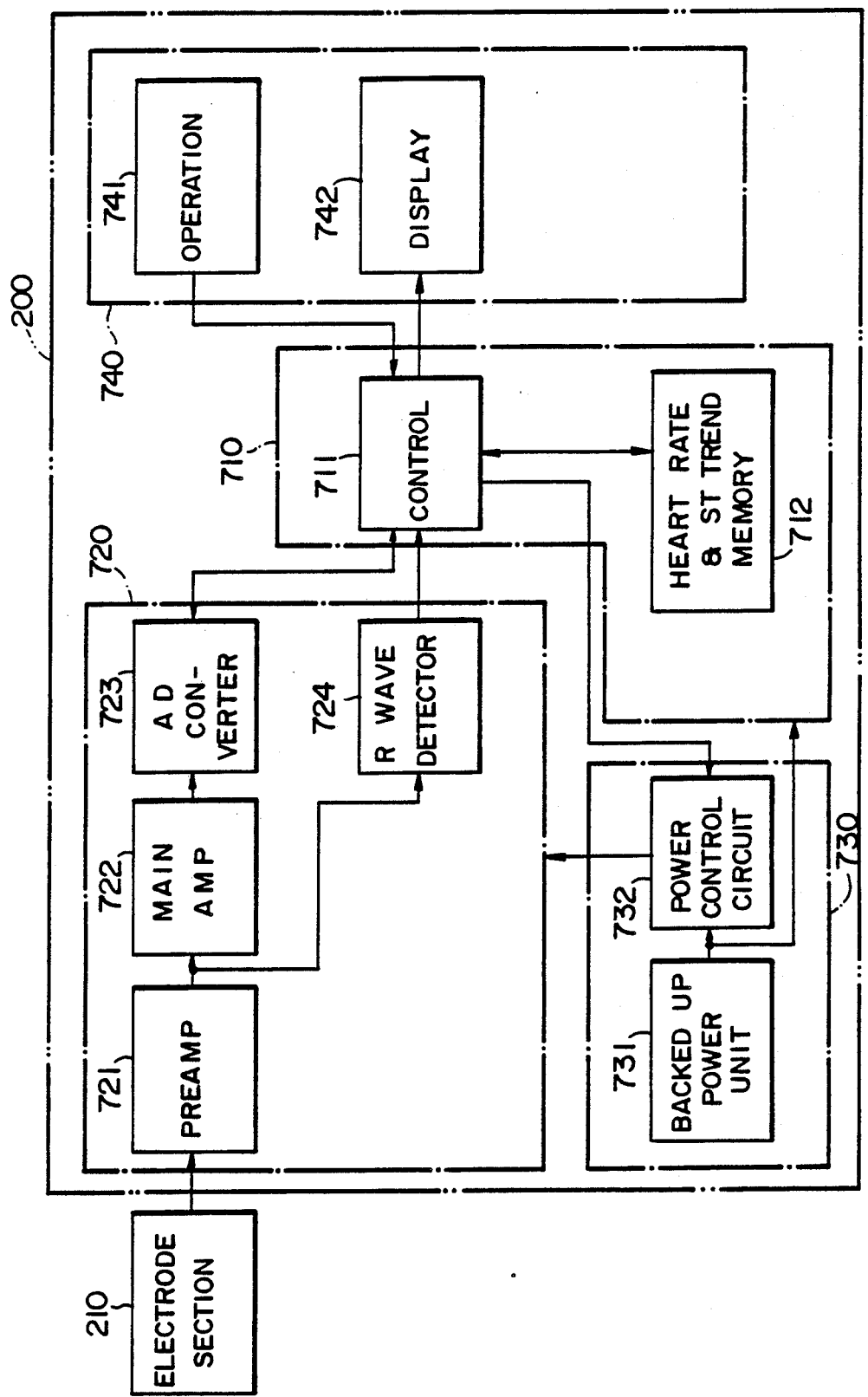

FIG. 13 is representative of still another alternative embodiment of the present invention in which the waveform memory 713 and event switch 215 of the embodiment shown in FIG. 12 are omitted. With this embodiment, therefore, there is not available the function of writing to the waveform memory 713 the waveform of an ECG signal which has appeared when the subject has pressed the event switch 215. More specifically, this embodiment is capable of recording only the heart rate and the ST value.

While the illustrative embodiments of the present invention have been shown and described in relation to a momentary heart rate trend and a momentary ST trend, it is sometimes more preferable to record averaged trends than to record momentary trends. The present invention is, therefore, not limited to the momentary heart rate trend and momentary ST trend.

In summary, in accordance with the present invention, electrocardiographic information to be recorded are composed of information associated with a heartbeat trendgram and an ST trendgram which are most effective for the diagnosis of an arrhythmia that occurs with a frequency of, e.g., 12 to 24 hours, and a complete electrocardiographic waveform appearing in the event when a subject feels a symptom. Hence, the capacity of a memory needed to record such information is noticeably reduced to in turn promote the use of a semiconductor memory, for example, in place of a cassette type magnetic tape. Further, a medical doctor has only to examine a minimum necessary amount of ECG information for screening which includes the complete waveform associated with a subjective symptom.

The present invention, therefore, improves the portability of an electrocardiograph to thereby free a subject from excessive restraint and loads, while saving the cost. In addition, the present invention reduces the analyzing time in the event of screening of a cardiac disorder and thereby the loads of a doctor, while enhancing accurate analysis.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

What is claimed is:

1. A long-term electrocardiograph for screening, comprising:
   input means for collecting an electrocardiogram signal from a subject;
   detector means for determining an R wave included in the electrocardiogram signal;
   processing means for processing the electrocardiogram signal in dependence upon the determining of the R wave by said detector means, to produce first data, representative of a momentary heart rate trendgram and a momentary ST trendgram, associated with the electrocardiogram signal; and
   first storage means for storing therein the first data time-serially under control of said processing means.

2. An electrocardiograph in accordance with claim 1, wherein said electrocardiograph is portable,
   wherein said electrocardiograph further comprises:
   operating means for entering at least one instruction manually; and
   second storage means for storing therein second data representative of a waveform of the electrocardiogram signal, and
   wherein said processing means responds to entering of the at least one instruction at a point in time by controlling storage, in said second storage means, of the second data associated with the electrocardiogram signal collected for a predetermined period of time preceding the point in time when the at least one instruction was entered.

3. An electrocardiograph in accordance with claim 2, wherein said second storage means comprises at least one ring buffer, operatively connected to said processing means and said operating means, for continuously storing the electrocardiogram signal received for a first predetermined period of time preceding current production of the electrocardiogram signal, and
   wherein said processing means discontinues storage of the electrocardiogram signal in the at least one ring buffer a second predetermined period of time after the at least one instruction is entered, the second predetermined period of time being smaller than the first predetermined period of time.

4. An electrocardiograph in accordance with claim 3, wherein said comparator circuit changes the variable threshold in response to an amplitude of the R wave detected by said comparator circuit.

5. An electrocardiograph in accordance with claim 2, wherein said electrocardiograph is connectable to an output device for preparing visual representations of the momentary heart trendgram and the momentary ST trendgram represented by the first data, and
   wherein said electrocardiograph further comprises transferring means for connecting said processing means to the output device and for transferring the first data to the output device while connected to said processing means.

6. An electrocardiograph in accordance with claim 5, wherein said transferring means detachably connect said processing means to the output device.

7. An electrocardiograph in accordance with claim 5, wherein the output device includes a display for visually displaying the momentary heart rate trendgram, the momentary ST trendgram and a representation of the second data associated with the electrocardiogram signal, and
   wherein said transferring means further transfers the second data to the output device from said processing means while the output device is connected thereto.

8. An electrocardiograph in accordance with claim 1, wherein said input means comprises a plurality of electrodes installable on the subject,
   wherein said electrocardiograph further comprises error detection means for detecting error in installation of any of said plurality of electrodes on the subject, and
   wherein said processing means interrupts storage of the first data in said first storage means upon detection of error by said error detection means and said operating means, for continuously storing the electrocardiogram signal received for a first predetermined period of time preceding current production of the electrocardiogram signal, and
   wherein said processing means discontinues storage of the electrocardiogram signal in the at least one ring buffer a second predetermined period of time after the at least one instruction is entered, the second predetermined period of time being smaller than the first predetermined period of time.

9. An electrocardiograph in accordance with claim 1, wherein said detector means comprises:
   a filter, operatively connected to said input means, for producing a signal corresponding to the R wave;
   an absolute value circuit, operatively connected to said filter, for producing an absolute value of the R wave; and
   a comparator circuit, operatively connected to said absolute value circuit, having a variable threshold, for comparing the electrocardiogram signal with the variable threshold to detect the R wave, said comparator circuit changing the variable threshold in dependence upon the R wave.

* * * * *

UNITED STATES PATENT AND TRADEMARK OFFICE
CERTIFICATE OF CORRECTION

PATENT NO. : 5,058,597

DATED : October 22, 1991

INVENTOR(S) : Onoda et al.

It is certified that error appears in the above-identified patent and that said Letters Patent is hereby corrected as shown below:

Col. 5,  line 17, "S. T." should be --ST--.

Col. 6,  line 27, "valve" should be --value--.

Col. 12, line 37, "means and said" should be --means.--; lines 38-47 should be deleted.

Signed and Sealed this

Twenty-third Day of February, 1993

Attest:

STEPHEN G. KUNIN

*Attesting Officer*   Acting Commissioner of Patents and Trademarks